United States Patent [19]

Baggaley

[11] 4,410,327

[45] Oct. 18, 1983

[54] DIAPER

[75] Inventor: Norman E. Baggaley, Umhloti Beach, South Africa

[73] Assignee: Laboratories (South Africa)(Proprietary) Ltd., Johannesburg, South Africa

[21] Appl. No.: 252,551

[22] Filed: Apr. 9, 1981

[30] Foreign Application Priority Data

Apr. 14, 1980 [ZA] South Africa .................... 80/2210

[51] Int. Cl.³ .......................................... A41B 13/02
[52] U.S. Cl. ................................................... 604/391
[58] Field of Search ............... 128/284, 287, DIG. 15; 604/391, 385

[56] References Cited

U.S. PATENT DOCUMENTS

| | | | |
|---|---|---|---|
| 2,477,914 | 8/1949 | Webb | 128/284 |
| 2,494,312 | 1/1950 | Rodgen et al. | 128/284 |
| 3,081,772 | 3/1963 | Brooks et al. | 128/DIG. 15 |
| 3,150,664 | 9/1964 | Noel | 128/DIG. 15 |
| 3,538,914 | 11/1970 | Myers | 128/DIG. 15 |
| 3,955,575 | 5/1976 | Okuda | 128/DIG. 15 |
| 4,051,854 | 10/1977 | Aaron | 128/DIG. 15 |

*Primary Examiner*—C. Fred Rosenbaum
*Attorney, Agent, or Firm*—Lalos, Leeds, Keegan, Lett & Marsh

[57] ABSTRACT

A diaper incorporating quick release means in the form of strips of Velcro (trademark) tape. A body encircling edge of the diaper is provided with strips of the tape on both sides while the opposite edge is provided with complemental strips fixed directly to the diaper and on a flexible element. In use of the invention the strips of tape permit rapid location of the diaper on an infant's body and the diaper may thereafter be adjusted. The flexible element serves to reinforce the attachment.

14 Claims, 1 Drawing Figure

U.S. Patent    Oct. 18, 1983    4,410,327
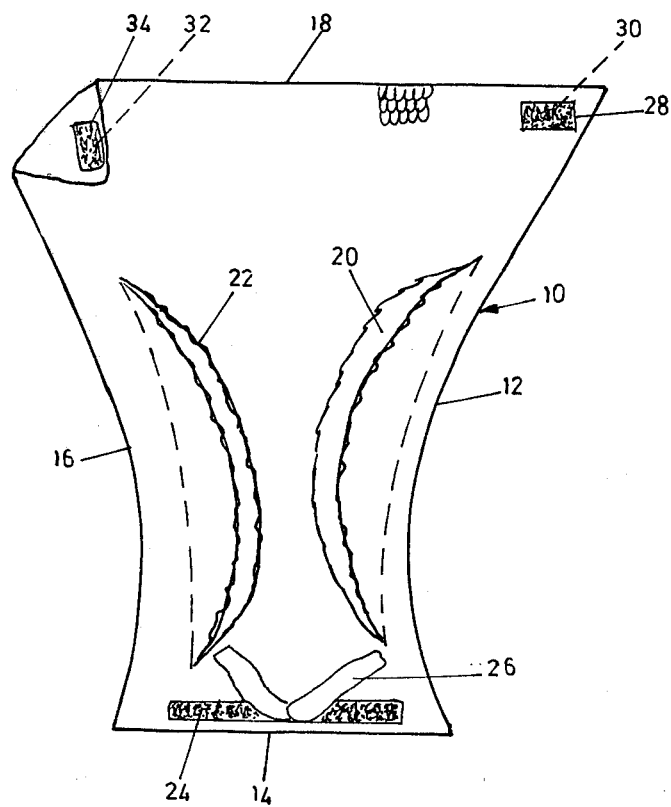

DIAPER

FIELD OF THE INVENTION

This invention relates to a diaper that is provided with fastening means thereon.

BACKGROUND TO THE INVENTION

It is known to provide diapers with fastening means such as VELCRO (Trade Mark) that facilitate securing of the diaper on a baby.

PRIOR ART

The prior art known to the Applicant is as follows: U.S. Pat. Nos. 2,004,088 Alsop, 3,081,772 Brooks et al, 3,089,494 Schwartz, 3,441,024 Ralph, 3,776,233 Schaar, 3,943,930 Schaar, 3,995,575 Okuda, 4,041,951 Sanford, 4,051,854 Aaron, 4,158,906 Watson, 4,241,462 Tagawa et al, and U.S. Pat. No. De. 249,280 Banuelos.

SUMMARY OF THE INVENTION

According to the invention a diaper includes first quick release means towards each end and on both sides of one body-encircling edge, complemental quick release means on the opposite edge and adapted to coact with the first means on the opposite side thereof, and a flexible element associated with the said opposite edge which flexible element includes quick release means complemental to the first means on the same side of the diaper.

In the preferred form of the invention the quick release means comprise strips of Velcro (trade mark) tape with the means at the said opposite edge comprising the complemental form of the means on the reverse side of the body-encircling edge and the quick release means on the flexible element being complemental to the form of the means at the body encircling edge on the same side as the flexible elements.

Preferably the diaper is in the form of a waisted rectangle of a suitably absorbent fabric. Darts are formed to effect this waisted portion and the diaper has two broad edges. The complemental parts of a strip of Velcro (Trade Mark) tape is sewn along one of the broad edges of the diaper. At the corner of the other edges of the diaper and on both surfaces are sewn four short strips of the tape. Two of these engage with the strip on the opposite side and the complemental strip from the latter side engages the two short strips on the opposite face for a double connection. The flexible element may comprise a tape attached at its centre and having Velcro forms at either end to complement the Velcro at the corners of the same side of the diaper.

BRIEF DESCRIPTION OF THE DRAWING

The drawing illustrates a view of a diaper according to the invention.

DESCRIPTION OF A PREFERRED EMBODIMENT OF THE INVENTION

A diaper comprises a rectangular piece of linen 10 having edges 12, 14, 16 and 18. The edges 12 and 16 are equal in length while the edge 14 is shorter in length than the edge 18.

The linen 10 is a double layered material that is folded along the edge 18 and sewn along the edges 12, 14 and 16. Two elongated darts 20 and 22 are formed along the edges 12 and 16 such that the linen 10 has substantially crescent shaped formations along these edges.

Strips 24 and 26 are complemental parts of a length of Velcro (Trade Mark) tapes and are sewn along the edge 14. The strip 24 is attached along all its edges to the linen 10 while the strip 26 is sewn along its width at its centre. At the corners of the edge 18 are sewn pieces of Velcro (Trade Mark) tape 28 and 32 on one surface of the material and pieces 30 and 34 on the opposite surface. In use the surface of the material 10 of the diaper as seen in the drawing forms the outer portion of the diaper, when in the position. A baby is made to lay in the supine position with the hip region of the baby being located in the region of the edge 18 and the thighs located across the edges 12 and 16. It will be appreciated that a baby lying in this position will be kicking its legs about thus hampering the location of the diaper on the baby. The strip 24 is brought into engagement with the strip 30 and the strip 34. Having temporarily located the diaper on the baby, each of the strips 30 and 34 are adjusted to properly position the diaper on the baby. Thereafter the strip 26 is finally brought into engagement with the strips 28 and 32 and with the strip 24 thus completing the fastening of the diaper.

An advantage of the diaper is that the darts 20 and 22 provide an enclosure for excreta to collect thus preventing any escape from the area covered by the diaper. The darts 20 and 22 also provide a crescent shaped formation to accommodate the thighs of the baby. Furthermore, use of the Velcro (Trade Mark) tape has the advantage of allowing for adjustment of the diaper on the baby's body after initial location. The Velcro (Trade Mark) tape is durable and suitable adapted to for successive uses of the diaper. A further advantage of the diaper is that the edge 18 is not sewn and the linen 10 retains its elasticity in this region.

I claim:
1. A diaper comprising:
   a body of material having a first edge adapted to encircle an infant, a second edge opposite said first edge, a first side, and a second side opposite said first side,
   a first quick release means attached to said first said generally adjacent said first edge,
   a second quick release means attached to said second side generally adjacent said first edge,
   a third quick release means attached to said first side generally adjacent said second edge and adapted to coact with said second quick release means, and
   a flexible element associated with said second edge, and including a fourth quick release means adapted to coact with said first quick release means.
2. The diaper according to claim 1 including,
   said flexible element comprising an elongated strip of material connected to said body of material at a mid-point of said strip and thereby having two free ends,
   said fourth quick release means being attached to said free ends.
3. The diaper according to claim 2 including,
   said fourth and first quick release means reinforcing the engagement of said third and second quick release means.
4. The diaper according to claim 2 including,
   said first quick release means being attached to the corners of said first edge.
5. The diaper according to claim 1 including, said first, second, third, and fourth quick release means comprising a Velcro means.

6. The diaper according to claim 2 including, each said first, second, third, and fourth quick release means comprising a Velcro means.

7. The diaper according to claim 1 including, said body of material including a double layered material.

8. The diaper according to claim 7 including, said double layered material being folded along said first edge, and said body of material having a generally rectangular shape including said first edge, said second edge, a third edge and a fourth edge, the two layers being joined only along said second, third, and fourth edges.

9. The diaper according to claim 7 including, said double layered material including a pair of darts disposed generally perpendicular to said first edge.

10. The diaper according to claim 9 including, said pair of darts comprising a pair of opposed crescent shaped darts.

11. A diaper comprising:
a body of material having a first edge adapted to encircle an infant, a second edge opposite said first edge, a first side, and a second side opposite said first side,
a second quick release means attached to said second side generally adjacent said first edge,
a third quick release means attached to said first side generally adjacent said second edge and adapted to coact with said second quick release means,
a reinforcing means attached generally adjacent said first and second edges for reinforcing the engagement of said second and third quick release means,
said reinforcing means including a first quick release means attached to said first edge, and
a flexible element associated with said second edge and including a fourth quick release means adapted to coact with said first quick release means.

12. The diaper according to claim 11 including, said flexible element comprising an elongated strip of material connected to said body of material at a mid-point of said strip and thereby having two free ends,
said fourth quick release means being attached to said free ends.

13. The diaper according to claim 11 including, said first quick release means being attached to the corners of said first edge.

14. The diaper according to claim 11 including, each said first, second, third, and fourth quick release means comprising a Velcro means.

* * * * *

UNITED STATES PATENT AND TRADEMARK OFFICE
CERTIFICATE OF CORRECTION

PATENT NO. : 4,410,327
DATED : October 18, 1983
INVENTOR(S) : NORMAN E. BAGGALEY It is certified that error appears in the above-identified patent and that said Letters Patent is hereby corrected as shown below:

On the Data Cover Sheet, "[73] Assignee: Laboratories (South Africa) (Proprietary) Ltd., Johannesburg, South Africa" should read -- [73] Assignee: De-Nol Laboratories (South Africa) (Proprietary) Limited, Johannesburg, Republic of South Africa --.

Signed and Sealed this

Twenty-third Day of October 1984

[SEAL]

Attest:

*Attesting Officer*

GERALD J. MOSSINGHOFF

*Commissioner of Patents and Trademarks*